United States Patent [19]

Goldsmid

[11] 4,324,129

[45] Apr. 13, 1982

[54] METHOD AND MEANS FOR DISTINGUISHING GEMSTONES

[75] Inventor: Hiroshi J. Goldsmid, Beecroft, Australia

[73] Assignee: Unisearch Limited, Kensington, Australia

[21] Appl. No.: 131,352

[22] Filed: Mar. 18, 1980

[30] Foreign Application Priority Data

Mar. 28, 1979 [AU] Australia .............................. PD8221

[51] Int. Cl.³ .......................................... G01N 25/18
[52] U.S. Cl. ................................................. 73/15 A
[58] Field of Search ............................. 73/15 R, 15 A

[56] References Cited

U.S. PATENT DOCUMENTS

| | | |
|---|---|---|
| 2,330,599 | 9/1943 | Kuehni ..................... 73/15 |
| 2,951,360 | 9/1960 | Sampson et al. ........... 73/15 |
| 3,611,786 | 10/1971 | Schorr ..................... 73/15 |
| 3,668,927 | 6/1972 | Howell et al. ............ 73/15 |
| 4,255,962 | 3/1981 | Ashman ................... 73/15 A |

FOREIGN PATENT DOCUMENTS 855658 12/1960 United Kingdom .................... 73/15
1036124 7/1966 United Kingdom .................... 73/15

OTHER PUBLICATIONS

"A Pulsed Thermal Comparator for the Schulte Measurement of Thermal Conductivity" in Proc. of the 9 Conf. on Thermal Conductivity, pp. 589-598, 10/69.

*Primary Examiner*—Herbert Goldstein
*Attorney, Agent, or Firm*—Michael J. Striker

[57] ABSTRACT

A method of identifying a material, such as a gemstone by applying a thermocouple to a stone, the thermocouple comprising two dissimilar metals having junctions spaced close to each other, heating one of said junctions, applying the other junction to the stone via a high thermal conducting tip and, recording the thermoelectric e.m.f. developed between the junctions which recorded value provides a determination of the type of material.

7 Claims, 3 Drawing Figures

METHOD AND MEANS FOR DISTINGUISHING GEMSTONES

BACKGROUND OF THE INVENTION

The present invention relates to a method and means for comparing materials in terms of their thermal conductivities, and more particularly for distinguishing gemstones which may only be supplied in very small samples.

SUMMARY OF THE INVENTION

In one form the method of the invention comprises identifying a material by determining its thermal conductivity, including applying a thermocouple to the material to be tested, said thermocouple comprising two dissimilar metals having junctions spaced close to each other, continuously supplying heat to one of said junctions at least up to just prior to making contact between the other junction and said material and pressing a high termal conductivity tip at the other junction into contact with said material so that heat flows through at least part of one of the thermocouple branches, recording the thermoelectric e.m.f. developed between said junctions, and identifying the material by reference to the maximum thermoelectric e.m.f. or to the rate of change of e.m.f.

In another form the present invention provides a thermal comparator for use in identifying materials such as gemstones, said comparator comprising a thermocouple between two dissimilar metals and having two junctions, one branch of the thermocouple forming the main source of heat for a short period of time after a high thermal conductivity tip at one of said junctions is placed in contact with the material to be identified.

By using a thermal comparator as above defined it can be seen that as an approximation, the maximum temperature difference over the thermocouple is determined by the ratio of thermal resistance of the branch of the thermocouple between the junctions to the thermal resistance of the interface between the contacting tip and the test material. The latter is a function of the thermal conductivity of the test material provided that the area of contact is sensibly constant.

In an embodiment of the comparator of the invention, the short branch of the thermocouple has been a piece of copper wire of about 0.3 mm diameter and about 1 cm in length, the rest of the thermocouple has consisted of constantan wires of about the same diameter. The constantan wires have been coiled to provide a spring inside a glass tube of about 3 mm internal diameter. The copper wire has been allowed to project beyond the constantan at the junction held against the material to be identified so that the interface has always been between copper and the test material. It has been arranged that the amount of movement against the spring on making contact always has the same value. In one arrangement the whole device has been heated and removed from the source of heat before placing the junction in contact with the material. The resultant e.m.f. depends on the thermal conductivity of the test material. Additionally, where the contacting junction has a low thermal capacitance the comparator is particularly suited for identifying small samples of material. In another arrangement the junction remote from the test material has been continuously heated by means of a small electrical heater.

Use of apparatus of this invention is most beneficial in distinguishing diamond from other gemstones, which other gems have a similarly cubic structure and a closely approximating refractive index to that of diamond.

Other values of the present invention reside in that it entails the non-destructive assessment of samples which may only be available as very small samples.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DETAILED DESCRIPTION OF THE PREFERRED EMBODIMENTS

Figure 1:
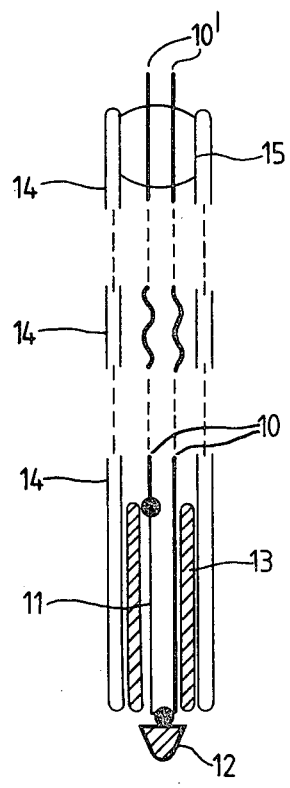
FIG. 1 is a schematic sectional view of a thermal comparator in accordance with the present invention.

In the comparator as shown in FIG. 1 a thermocouple is formed between two lengths of enamelled constantan wire 10 of 0.46 mm diameter and a short (10 mm) piece of copper wire 11 of 0.22 mm diameter. A conical copper head 12, of somewhat less than 1 mm$^3$ volume, is soldered to one of the thermocouple junctions. The copper wire 11 and the two junctions are held in a PVC sleeve 13, which can slide in a glass tube 14. The constantan wires 10 are cemented at 15 to the inside of one end of the glass tube and take a spiral form over part of their length. The point of the copper head 12 protrudes from the other end of the glass tube 14 by about 1 mm, but retract by this amount when the device is pressed against a hard surface, such as that of one of the gemstones. In experiments the free ends 10' of the constantan wires 10 were connected (via copper junctions at the same temperature) to a digital millivoltmeter (not shown); an instrument having a limit of resolution of not more than about 100 $\mu$V was used.

To use this comparator it was first placed in an environment at a specific elevated temperature. In one example a test tube resting in a beaker of boiling water was used and found that the comparator reached equilibrium with its surroundings after about two minutes. It was then lifted from the test tube and pressed the copper head 12 against the gemstone under test observing the maximum e.m.f. on the millivoltmeter. The rate of change of e.m.f. with time is perhaps a more sensitive measure of the thermal conductivity but the maximum e.m.f. is easier to determine. The Table summarises the values that were obtained with the different gemstones. Invariably diamond gave the largest e.m.f. and cubic zirconia invariably gave the smallest.

Figure 2:
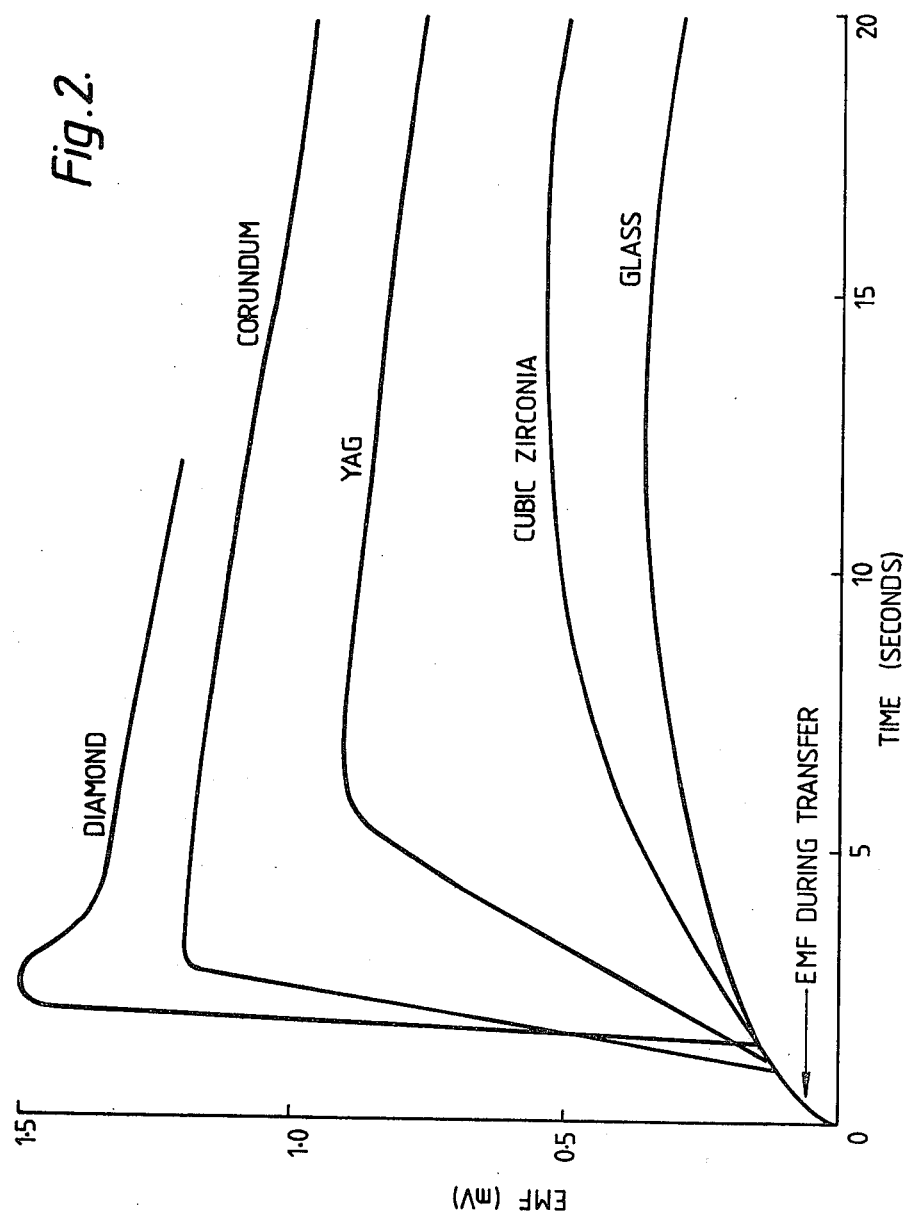
FIG. 2 is a graph showing the variation of e.m.f. with time in relation to various gemstones as sensed by the comparator of FIG. 1

The variation of e.m.f. with time was observed using a Tektronix Type 7623A storage oscilloscope with a plug-in amplifier Type 7A22. The behaviour of some of the gemstones and of a piece of glass is shown in FIG. 2. It is noted that there is very little development of the e.m.f. while the comparator is being transferred from the boiling water to the sample. Furthermore, the rapid rise of e.m.f. when contact is made to the sample, is usually followed by a rather slow decrease. It is thought that the maximum e.m.f. should correspond quite closely to the value that could be expected if the bulk of the gemstone were continually maintained at room temperature and the remote thermocouple junction were maintained at 100° C. Using Clark and Powell's equation 1962 J.Sci. Instrum. 39, 545–51 for the thermal resistance of the constriction, it was found that the results were consistent with a reasonable value for the contact radius of about $10^{-2}$ mm.

TABLE

Maximum e.m.f. from Thermal Comparator

| Sample | Thermal Conductivity* | Maximum e.m.f. mV W/mK Mean | Range of 5 readings |
|---|---|---|---|
| Diamond | 990–2320 | 1.56 | 1.47–1.63 |
| Corundum (synthetic) | 32–35 | 1.19 | 1.07–1.27 |
| Topaz | 19 | 1.01 | 0.97–1.06 |
| Zircon | 4.1–4.2 | 0.99 | 0.97–1.04 |
| Spinel (synthetic) | 12 | 0.83 | 0.74–0.96 |
| YAG+ | | 0.75 | 0.07–0.80 |
| Quartz | 5.9–11 | 0.75 | 0.67–0.82 |
| GGG++ | | 0.62 | 0.58–0.65 |
| Cubic zirconia | | 0.50 | 0.45–0.53 |

*Values near room temperature from CRC "Handbook of Chemistry and Physics" 57th Edition 1976-7.
+ Yttrium aluminium garnet
++ Gadolinium germanium garnet The heat source for the thermocouple wires may take the form of electrical resistance element cemented to the wires. A resistive heater may be employed in addition to or instead of indirect heating as described in the embodiment.

Figure 3:
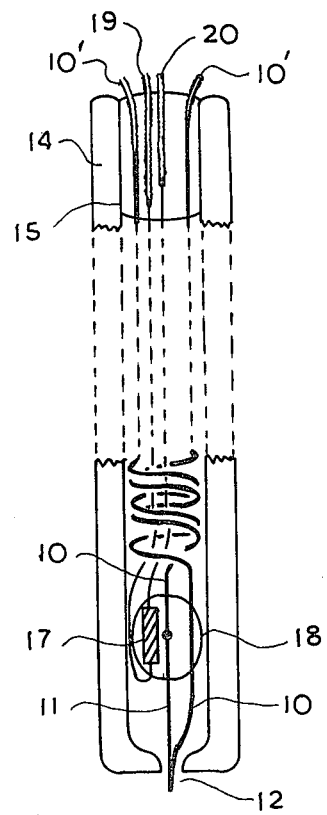
FIG. 3 is a schematic sectional view of a thermal comparator in accordance with another embodiment of the present invention.

FIG. 3 illustrates a modified form of the comparator shown in FIG. 1, wherein similar parts are numbered in similar manner as compared to those of FIG. 1. However, in this embodiment junction 12 is heated by an electrical resistance heater 17 cemented thereto by Analdite resin block 18. Heater 17 is operated by current flowing through leads 19, 20. In operation of this embodiment current should be applied to resistance heater for a sufficient time prior to using the comparator for testing the material so that the temperatures within the comparator have equilibrium values. Current can be continually applied to heater 17 via leads 19, 20 until the measurement is complete or it may be switched off when contact of the material with the tip 12 is made.

Further, the heating of the part of the thermocouple may be provided at the centre of this part rather than at the junction. If a heater circuit is provided it may incorporate a boosting device so that the comparator reaches its operating condition almost immediately.

The head 12 of the comparator may be of materials other than copper and may, for example, be of gold, platinum or other which may be more suited to particular applications of the invention.

It will be recognised by persons skilled in the art that numerous variations and modifications may be made to the invention as described above without departing from the spirit or scope of the invention as broadly described.

What is claimed is:

1. A method of identifying a material by determining its thermal conductivity, comprising the steps of applying to a material a thermocouple including two dissimilar metals and having junctions spaced relatively close to each other and forming thermocouple branches, and a high thermal conductivity tip at one of said junctions; continuously supplying heat to the other of said junctions at least up to just prior to making contact between said thermocouple and the material; pressing said tip at said one junction into contact with said material so that heat flows through at least part of one of the thermocouple branches; recording the thermoelectric e.m.f. developed between said junctions; and identifying the material by reference to the maximum thermoelectric e.m.f. or to the rate of change of e.m.f.

2. A thermal comparator for use in identifying materials such as gemstones, comprising a thermocouple to be applied to a material and including two dissimilar metals and having junctions spaced relatively close to each other and forming thermocouple branches and a high thermal conductivity tip at one of said junctions, one branch being connected to a source of heat at least up to just prior to making contact between the thermocouple and the material to be tested so that said one branch forms the main heat source for at least a short time after said tip at one of said junctions is placed in contact with the material to be identified.

3. The thermal comparator as claimed in claim 2, wherein said two dissimilar metals are copper and constantan.

4. The thermal comparator as claimed in claim 3, wherein said tip is made of copper.

5. The thermal comparator as claimed in claim 3, wherein said tip is made of metal selected from the group consisting of gold, silver, platinum or aluminum.

6. The thermal comparator of claim 4 or 5, wherein the thermocouple branch formed by constantan is in the form of coiled wire which acts as a spring to maintain a constant contact force between said tip and the material to be identified.

7. The thermal comparator as claim 9, wherein said source of heat includes an electrical resistor connected to at least one of said branches, said electrical resistor being operative when an electric current is passed therethrough.

* * * * *